(12) United States Patent
Watson

(10) Patent No.: US 8,022,368 B2
(45) Date of Patent: Sep. 20, 2011

(54) HYBRID METHOD FOR RANDOMS VARIANCE REDUCTION

(75) Inventor: Charles C. Watson, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 346 days.

(21) Appl. No.: 12/121,020

(22) Filed: May 15, 2008

(65) Prior Publication Data

US 2009/0072154 A1 Mar. 19, 2009

Related U.S. Application Data

(60) Provisional application No. 60/972,908, filed on Sep. 17, 2007.

(51) Int. Cl.
*G01T 1/164* (2006.01)
(52) U.S. Cl. .................................. 250/363.03

(58) Field of Classification Search .............. 250/363.03
See application file for complete search history.

(56) References Cited

OTHER PUBLICATIONS

Meikle, S. R. and R. D. Badawi. "Quantitative Techniques in PET." Positron Emission Tomography: Basic Science and Clinical Practice (2003): p. 91-114.*
Badawi et al. "Randoms Variance Reduction in 3D PET". Phys. Med. Biol. 44 (1999): p. 941-954.*

* cited by examiner

*Primary Examiner* — David Porta
*Assistant Examiner* — Casey Bryant
(74) *Attorney, Agent, or Firm* — Peter L. Kendall

(57) ABSTRACT

A method for reducing randoms variance in a Positron Emission Tomograph (PET) or Positron Emission Tomograph combined with another Medical Imaging device is disclosed. An average of an element of the randoms event (delayeds) sinogram may be estimated by dividing fan sums in delayeds sinogram by singles rates taken from headers of the delayeds sinogram.

16 Claims, 6 Drawing Sheets

HYBRID METHOD FOR RANDOMS VARIANCE REDUCTION

TECHNICAL FIELD

The technical field of the present disclosure relates to noise reduction in tomography. More particularly, a system and method of the present application allows a reduction of data variance due to randoms correction in positron emission tomography (PET).

BACKGROUND

Random coincidences are a significant source of noise in, for example, PET. The raw data collected by a PET scanner may be a list of coincidence events representing near-simultaneous detection of annihilation photons by a pair of detectors. Each coincidence event represents a line in space connecting two detectors along which the positron emission occurred. This line may be referred to as the line of response (LOR).

Coincidence events can be sorted into groups of LORs, called sinograms, that represent projection views through the radionuclide distribution within the object being scanned. The sinograms may be sorted by the angle of each view around the axis of the scanner, as well as its tilt with respect to this axis, the latter in the case of 3D acquisitions. A normal PET data set has millions of counts for the whole acquisition, which may include a large component of undesirable scatter and random events. Considerable pre-processing of the data may be required, for example, correction for random coincidences, estimation and subtraction of scattered photons, detector dead-time correction (after the detection of a photon, the detector must "cool down" again) and detector-sensitivity correction (for both inherent detector sensitivity and changes in sensitivity due to angle of incidence).

Consequently, there is considerable interest in developing methods and algorithms that reduce the data variance due to, for example, random coincidence correction. To arrive at the true events in a PET scanner, a subtraction of the random coincidences, measured using a delayed, or offset, coincidence window, from measured prompt coincidence events may be done. However, since random coincidences are statistically uncorrelated with the prompt coincidences, this subtraction will cause a random noise variance to be added to the corrected measured events. The amount of noise added during this correction will be proportional to the noise in the random coincidence estimate used. Thus this subtraction may make methods reducing noise in the estimated random coincidences attractive.

In view of the discussion above, there may be a need to provide a method and a system allowing for reduction of randoms variance. Further, these systems and methods should preferably be easy to implement and/or fast to compute.

It is always sought to improve the image quality in tomography. Consequently, a system and method reducing randoms variance may improve the final image quality in tomography.

Additionally, it may be desirable to provide a system and method that allows for a more accurate and precise reduction of randoms variance. A more accurate and precise reduction of randoms variance may be desirable from an economical and/or technical perspective.

SUMMARY

According to one embodiment a method may reduce randoms variance in a Positron Emission Tomograph (PET) or Positron Emission Tomograph combined with another Medical Imaging device. An averaged estimate of an element, $R_{ij}$, of the randoms event (delayeds) sinogram corresponding to detectors $i$ and $j$ in a detector ring of the PET or PET/Medical Imaging device may be expressed as $$\hat{R}_{ij} = \frac{R_i R_j}{2\tau \left(\sum_{i' \in I_j} s_{i'}\right)\left(\sum_{j' \in J_i} s_{j'}\right)}$$

wherein $R_i$ and $R_j$ are fan sums for detectors $i$ and $j$; $2\tau$ is the coincidence time window; the randoms relate to single event rates $s_i$ and $s_j$ in the detectors by $R_{ij}=2\tau s_i s_j$; $I_j$ is a set of detectors corresponding to the fan of detector $j$; and $J_i$ is a set of detectors corresponding to the fan of detector $i$. The embodiment may comprise the steps of estimating the numerator from fan sums in the delayeds sinogram of the PET or PET/Medical Imaging device; and estimating the denominator from singles rates taken from the header of the sinogram, or otherwise recorded.

According to further embodiments, estimating the denominator from singles rates taken from the header of the sinogram may be done by averaging and/or interpolating the single rates over several detectors. The several detectors may be arranged as multiplexed groups known as buckets, and/or rings.

According to a further embodiment, the averaged estimate of $R_{ij}$ may be used to correct for effects of randoms events in the PET or PET/Medical Imaging device.

According to one embodiment, a system for reducing randoms variance in a Positron Emission Tomograph (PET) or Positron Emission Tomograph combined with another Medical Imaging device, may include detectors arranged in a detector ring in the PET or PET/Medical Imaging device; means for generating sinograms; and processing means. The processing means may be operable to express an averaged estimate of an element, $R_{ij}$, of the randoms event (delayeds) sinogram corresponding to the detectors $i$ and $j$ in the detector ring of the PET or PET/Medical Imaging device as $$\hat{R}_{ij} = \frac{R_i R_j}{2\tau \left(\sum_{i' \in I_j} s_{i'}\right)\left(\sum_{j' \in J_i} s_{j'}\right)}$$

wherein $R_i$ and $R_j$ are fan sums for detectors $i$ and $j$; $2\tau$ is the coincidence time window; the randoms relate to single rates $s_i$ and $s_j$ in the detectors by $R_{ij}=2\tau s_i s_j$; $I_j$ is a set of detectors corresponding to the fan of detector $j$; and $J_i$ is a set of detectors corresponding to the fan of detector $i$. The processing means may be further operable to estimate the numerator from fan sums in the delayeds sinogram of the PET or PET/Medical Imaging device; and estimate the denominator from singles rates taken from the header of the sinogram, or otherwise recorded.

According to further embodiments, the processing means may be further operable to estimate the denominator from singles rates taken from the header of the sinogram by averaging and/or interpolating the single rates over several detectors. The several detectors may be arranged as buckets and/or rings.

According to a further embodiment, the processing means may be further operable to use the averaged estimate of $R_{ij}$ to correct for the effects of randoms events in the PET or PET/Medical Imaging device.

According to one embodiment, a method may reduce randoms variance in a Positron Emission Tomograph (PET) or Positron Emission Tomograph combined with another Medical Imaging device. An average of an element of the randoms event (delayeds) sinogram may be estimated by dividing fan sums in delayeds sinogram by singles rates taken from the header of the sinogram, or otherwise recorded.

According to further embodiments, the singles rates taken from the header of the sinogram may be averaged and/or interpolated single rates over several detectors. The several detectors may be arranged as buckets and/or rings.

According to a further embodiment, the averaged estimate of the element may be used to correct for effects of randoms events in the PET or PET/Medical Imaging device.

At least one of the embodiments may provide a system and method allowing for reduction of randoms variance that is easy to implement and/or fast to compute. Furthermore, at least one of the embodiments may improve the image quality in tomography.

Additionally, at least one of the embodiments may provide a system and method that allows for a more accurate and precise reduction of randoms variance from an economical and/or technical perspective.

The herein described systems and methods relate to reduction of randoms variance for PET. However, the herein described systems and methods may also apply to positron emission tomography combined with another Medical Imaging device, and/or other forms of tomography involving reduction of randoms variance.

The other Medical Imaging device in all embodiments may be, for example, an X-ray Computed Tomography scanner (PET/CT) or a Magnetic Resonance Imaging device (MRI).

Other technical advantages of the present disclosure will be readily apparent to one skilled in the art from the following description and claims. Various embodiments of the present application obtain only a subset of the advantages set forth. No one advantage is critical to the embodiments. Any claimed embodiment may be technically combined with any other claimed embodiment(s).

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain, by way of example, the principles of the invention.

DETAILED DESCRIPTION

Figure 1:
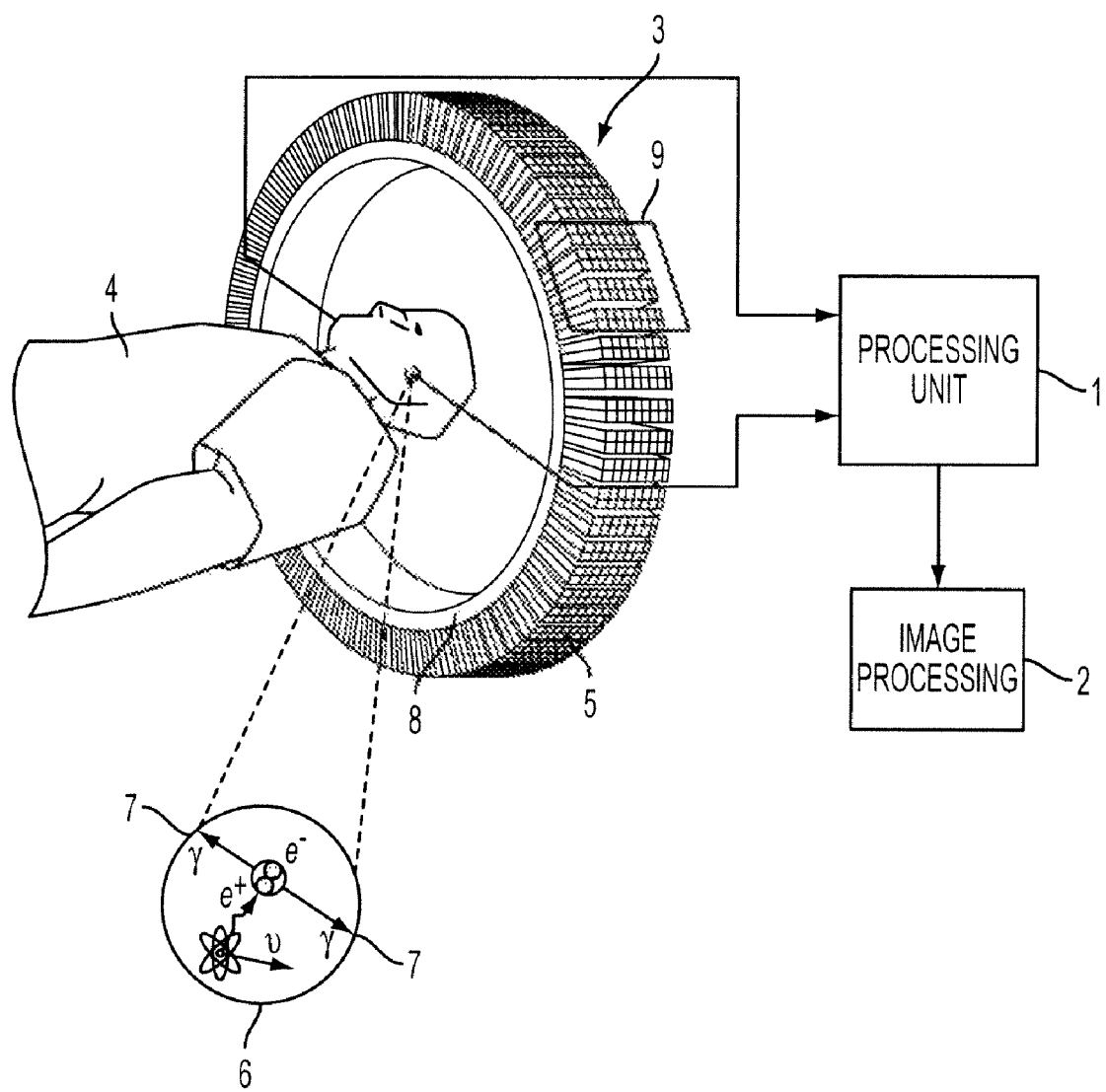
FIG. 1 shows an embodiment of processing principles of a PET.

FIG. 1 shows an embodiment of processing principles of a PET. A subject 4, for example a patient, is positioned within a detector ring 3 comprising photo-multiplier tubes (PMTs) 5. In front of the PMTs 5 are individual crystals 8, also called detectors 8. A group of four PMTs may have an array of detectors 8 in front of them. For example, an array of eight by eight or thirteen by thirteen detectors 8 (crystals) is possible, but any other array may be selected. Each detector 8 may be an individual crystal in front of respective PMT. During an annihilation process two photons 7 are emitted in diametrically opposing directions as schematically illustrated in circle 6. These photons 7 are registered by the PET as they arrive at detectors 8 in the detector ring 3. After the registration, the data, resulting from the photons 7 arriving at the detectors 8, may be forwarded to a processing unit 1 which decides if two registered events are selected as a so-called coincidence event. All coincidences are forwarded to the image processing unit 2 where the final image data may be produced via mathematical image reconstruction methods. Before the data can be used by such a reconstruction method the random variance may be reduced to exclude registered events that are not true events. A way of approaching this may be to subtract the random coincidences from the measured events. Hereby only the true events should remain.

A PET scanner may register a detected coincidence event in either a prompt coincidence time window or a delayed coincidence time window. The delayed coincidences represent random (accidental coincidence) events, and the prompt coincidences represent true coincidences contaminated by random events and other events, such as for example scatter. The prompt data may be corrected for the effects of the random events by subtracting the delayed coincidences. Such a subtraction compensates for the random events in terms of the mean but increases the variance data. By estimating the mean of random events from the delayeds sinogram, these estimates may be incorporated to create an estimated smoothed randoms sinogram useful for later image reconstruction.

Figure 2:
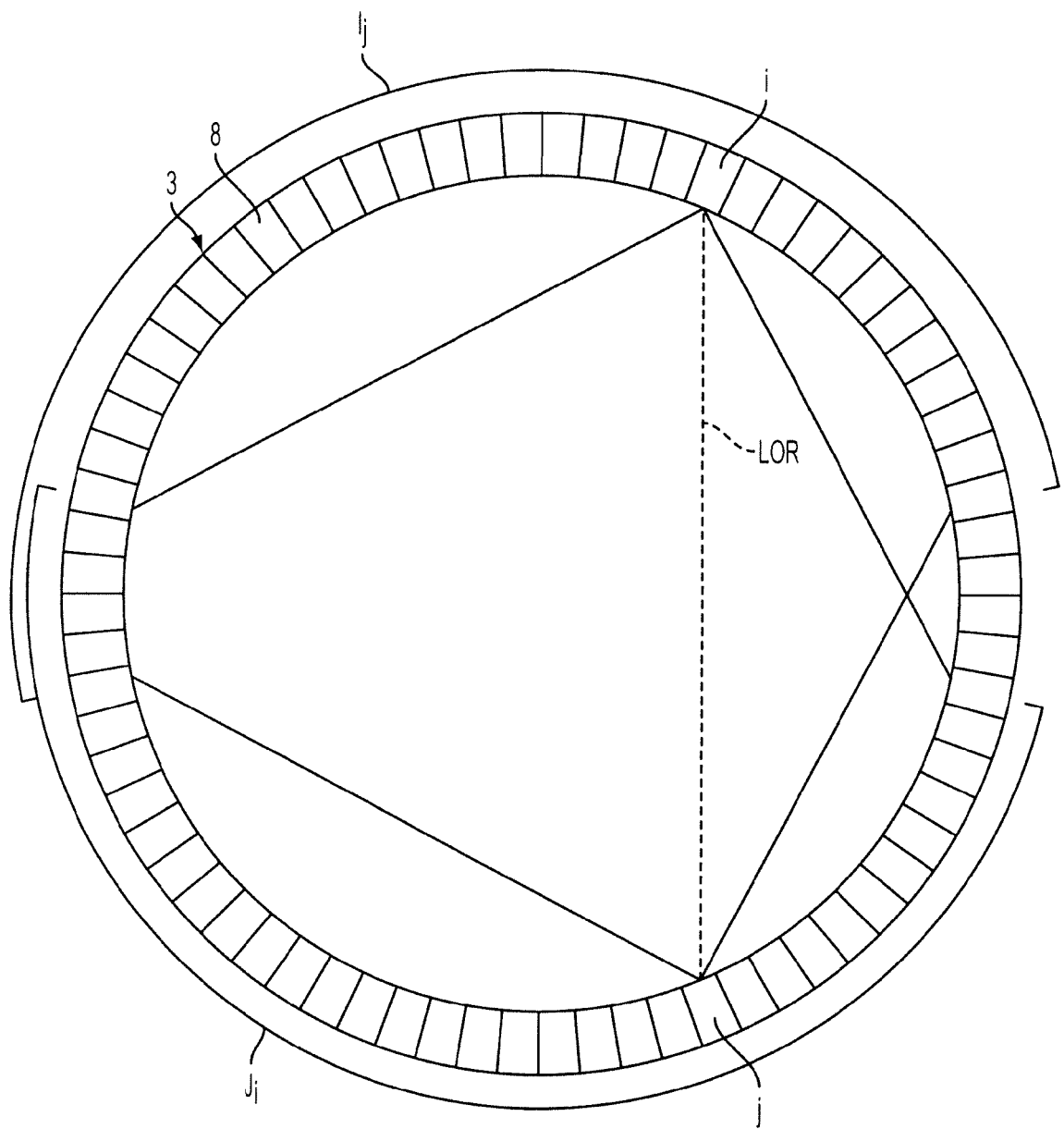
FIG. 2 shows and embodiment of detector fans for two detectors defining one LOR.

One exemplary method is described with reference to FIG. 2. FIG. 2 shows an embodiment with detector fans for two detectors $i$ and $j$ defining one LOR. A number of detectors 8 form the detector ring 3. Looking at any one detector, for example $i$ in FIG. 2, data may be collected for that detector in coincidence with many other detectors. This is what is referred to as a fan. In other words, all the detectors for which coincidences are measured with the detector $i$ are called the fan for detector $i$. The fan sum is then the sum of all data collected by this set of detectors. In FIG. 2 the set of detectors 8 making up the fan for detector $i$ is marked $J_i$. The set of detectors 8 making up the fan for detector $j$ is marked $I_j$.

Let $R_{ij}$ be an element of the randoms (delayeds) sinogram corresponding to detectors $i$ and $j$. Assume that the randoms are related to the singles rates $s_i$ and $s_j$ in the detectors by:

$$R_{ij} = 2\tau s_i s_j \qquad (1)$$

where $2\tau$ is the coincidence time window. Let $I_j$ be the set of detectors for which there are LORs in the sinogram terminating at j, i.e., the fan of j. Similarly, let $J_i$ be the fan of i. Then the fan sums for i and j are:

$$R_i = \sum_{j' \in J_i} R_{ij'} = \sum_{j' \in J_i} 2\tau s_i s_{j'} = 2\tau s_i \sum_{j' \in J_i} s_{j'} \qquad (2)$$

$$R_j = \sum_{i' \in I_j} R_{i'j} = \sum_{i' \in I_j} 2\tau s_{i'} s_j = 2\tau s_j \sum_{i' \in I_j} s_{i'}$$

Solving these two relations for $s_i$ and $s_j$, and substituting into equation (1), we have an expression for an averaged estimate of $R_{ij}$ $$\hat{R}_{ij} = \frac{R_i R_j}{2\tau \left( \sum_{i' \in I_j} s_{i'} \right) \left( \sum_{j' \in J_i} s_{j'} \right)} \quad (3)$$

Unfortunately, without further constraints or approximations the denominator in equation (3) cannot be expressed directly in terms of sums over $R_{ij}$. At least two approaches may be suggested to address this issue.

The first approach may be to assume that the sums in the denominator do not vary appreciably and replace them with a constant factor. This suggested "fan sum" approach is an approximate solution.

The second approach may be that an exact solution can be obtained by constraining $I_j$ and $J_i$, such that they are fixed groups of detectors (i.e. do not vary with the $i$ or $j$ detectors within them), and further, such that each detector in one group is in coincidence with every detector in the other group (all possible LORs between the two groups are measured). In this "block" sum approach, the expression for the randoms estimate becomes $$\hat{R}_{A_i B_j} = \frac{R_i R_j}{\sum_{i'} \sum_{j'} R_{i'j'}} \quad (4)$$

Although the suggested block sum method may be exact, it has the drawback that it does not use all available data for the estimate. Consequently, the full potential of the randoms smoothing effect is not realized.

A more sophisticated suggestion relating to this approach may be to permit the use of multiple pairs of blocks of detectors for the estimation, thereby improving the smoothing effect. Nevertheless, even such a technique still not takes full advantage of all the data available for the estimation.

Returning to equation (3), the unconstrained sums in the denominator may be the sums of the singles rates over the detectors in the two fans. A PET scanner may have the capability of recording the singles rates in its detectors, at least at a coarse-grained level. The fan of any one detector may be the half of all the detectors, typically the half directly across from the detector of interest. The drawback of only having coarse-grained data is thus reduced, because, when considering half of the available data, using fine resolution of the singles rate rather than coarse-grained data may not be significant.

A sinogram may comprise two files, for example, a binary data file and an ASCII header file. The binary data file may record the coincidence events detected in each LOR, for both the prompt and delayed coincidence windows. The header of a sinogram may comprise additional data, such as date and time of scan, duration of scan, information on singles rates, etc. In some realizations, these two component files may be combined into a single file containing a header part and a binary data part. In other realizations, the binary data are not organized into sinograms, but are recorded in time sequence of their measurement. This may be referred to as a listmode file. Listmode format data may be histogrammed into sinogram format as needed. Other organizations of the data are also possible Since the fan is typically half a ring, the averaging of the singles entailed may be a fairly accurate and robust estimation of the denominator of equation (3). Furthermore, on certain tomographs data of the singles rate for estimating the denominator in equation (3) may be available at, for example, a bucket block-ring level (one rate averaged over each block ring in each bucket). For example, an array of four by four blocks of PMTs may form one bucket and a certain amount of buckets, for example sixteen buckets, may form one detector ring unit. The number of detectors in a block, the number of blocks in a bucket, and the number of buckets in a detector ring unit may differ from tomograph to tomograph. For example an eight by eight (or thirteen by thirteen) array of detectors (crystals) may form one block of detectors. Four PMTs may be behind each block. For example sixteen blocks may be called a bucket. In a tomograph with four rings of block detectors, the bucket 9 may extend over four rings axially and over four blocks radially. An example of such a bucket 9 is shown in FIG. 1. Thus, a bucket block ring may refer to the average across four blocks that are in one bucket and in one of the four block rings. The single rates may be averaged over several detectors 8 and interpolations may be made when the fan spans over parts of buckets.

With reference to equation (3), the numerator may express the fan sums for detectors $i$ and $j$. These fan sums may be estimated from fan sums in the delayed sinogram.

Consequently, in an embodiment, a method or a system for reducing randoms variance may comprise that the numerator in equation (3) may be estimated from fan sums in the delayeds sinogram, while the denominator may be estimated from the singles rates taken from the sinogram header. This hybrid method has the advantage that it uses all available data in both the delayeds sinogram and single rates to estimate a given randoms rate.

Although theoretically equation (3) is an exact method, there may be some residual error due to the coarse-graining of the singles. However, the method or the system may be more accurate than the suggested fan sum approach, and may be more precise than the suggested block sum approach.

The method is easy to implement and very fast to compute because the method works with data already present and available. At least one embodiment based on this method may improve the image quality in a tomography, because more measured data is used for reducing the randoms variance.

The system is easy to implement and very fast to compute because the system works with data already present and available. At least one embodiment based on this system may improve the image quality in a tomography, because more measured data is used for reducing the randoms variance.

One embodiment may show an example of how a smoothed randoms sinogram using an embodiment of the method or the system may be generated. Further such a smoothed randoms sinogram may be compared to a measured randoms sinogram. In the embodiment, single event rates may be read from the header of the sinogram data files that result from a PET acquisition. These singles values may be interpolated to estimate a singles rate $s_i$ for each detector in the scanner. Maps, for example in the form of tables or arrays of numbers, relating each sinogram bin to the two corresponding detectors may be generated. Using these maps, for each detector the fan sum of delayed coincidences in the measured sinogram is formed as:

$$R_i = \sum_{j' \in J_i} R_{ij'} \quad (5)$$

The corresponding sum over all singles rates in the fan may also be computed as:

$$\sigma_i = \sum_{j' \in J_i} s_{j'} \qquad (6)$$

For each detector, the ratio of these two quantities may be formed as:

$$\rho_i = \frac{R_i}{\sigma_i} = \frac{\sum_{j' \in J_i} R_{ij'}}{\sum_{j' \in J_i} s_{j'}} \qquad (7)$$

Then the value for each bin in the output smoothed randoms sinogram is estimated by taking the product of the two corresponding values of $\rho_i$. The sinogram may be indexed by a radial bin index b and a projection angle index a. Each sinogram bin then corresponds to two detectors, i(a,b) and j(a,b). A preliminary estimated smoothed randoms rate for this bin is then estimated by $$\hat{R}'_{a,b} = \rho_{i(a,b)} \rho_{j(a,b)} \qquad (8)$$

To account for the 2T factor, and any numerical imprecision, this estimate may then be scaled by a single multiplicative factor chosen so that the total of the estimated smoothed randoms is equal to the sum of the measured delayed coincidences in the sinogram. The final estimate of the smoothed randoms sinogram may then be $$\hat{R}_{a,b} = \alpha \hat{R}'_{a,b}, \qquad (9)$$

where $$\alpha = \frac{\sum_{i,j} R_{i,j}}{\sum_{a,b} \hat{R}'_{a,b}} \qquad (10)$$

Figure 3:
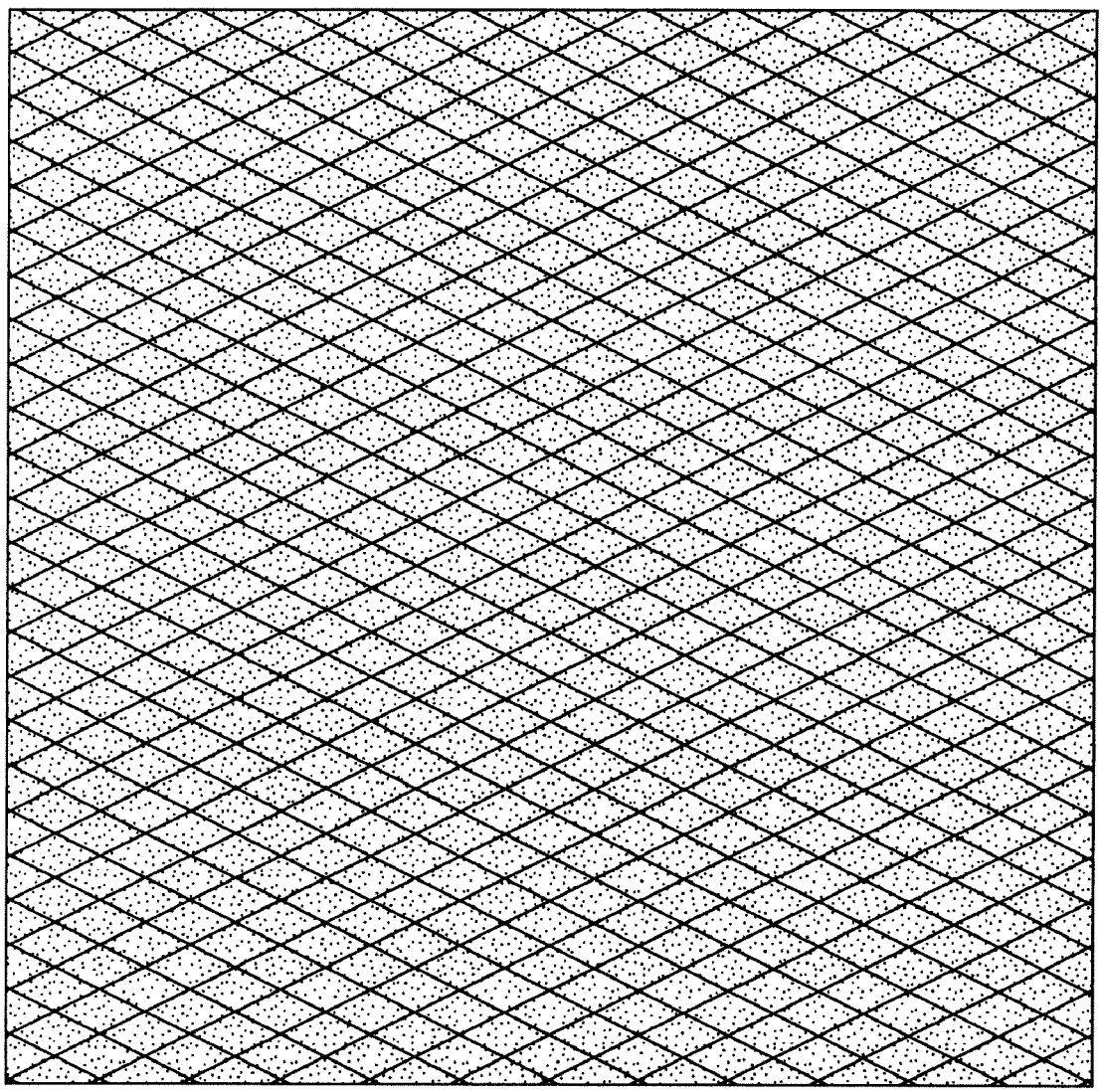
FIG. 3 shows an example of a measured randoms sinogram.
Figure 4:
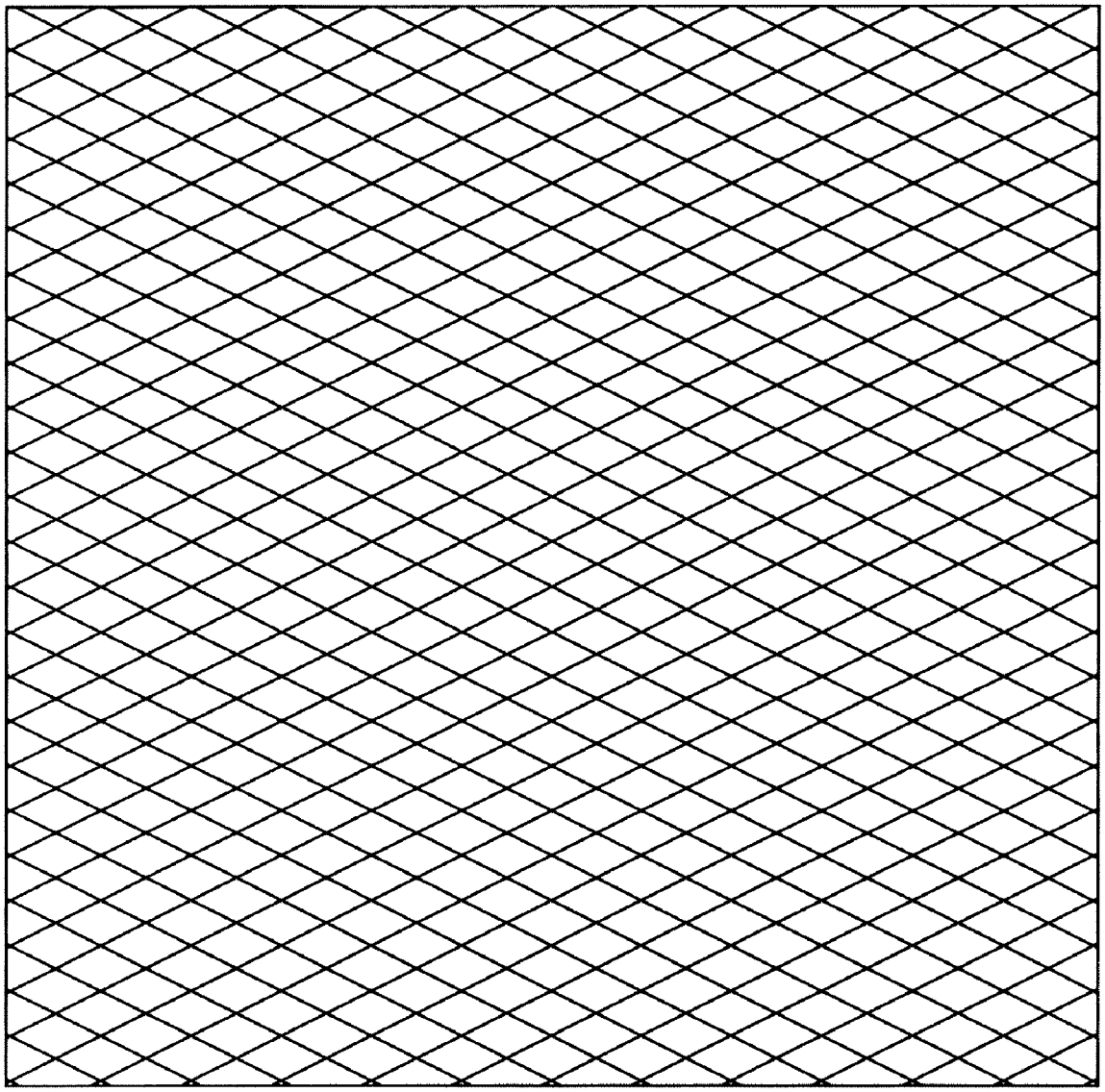
FIG. 4 shows an example of an estimated smoothed randoms sinogram generated by using an embodiment of the method.
Figure 5:
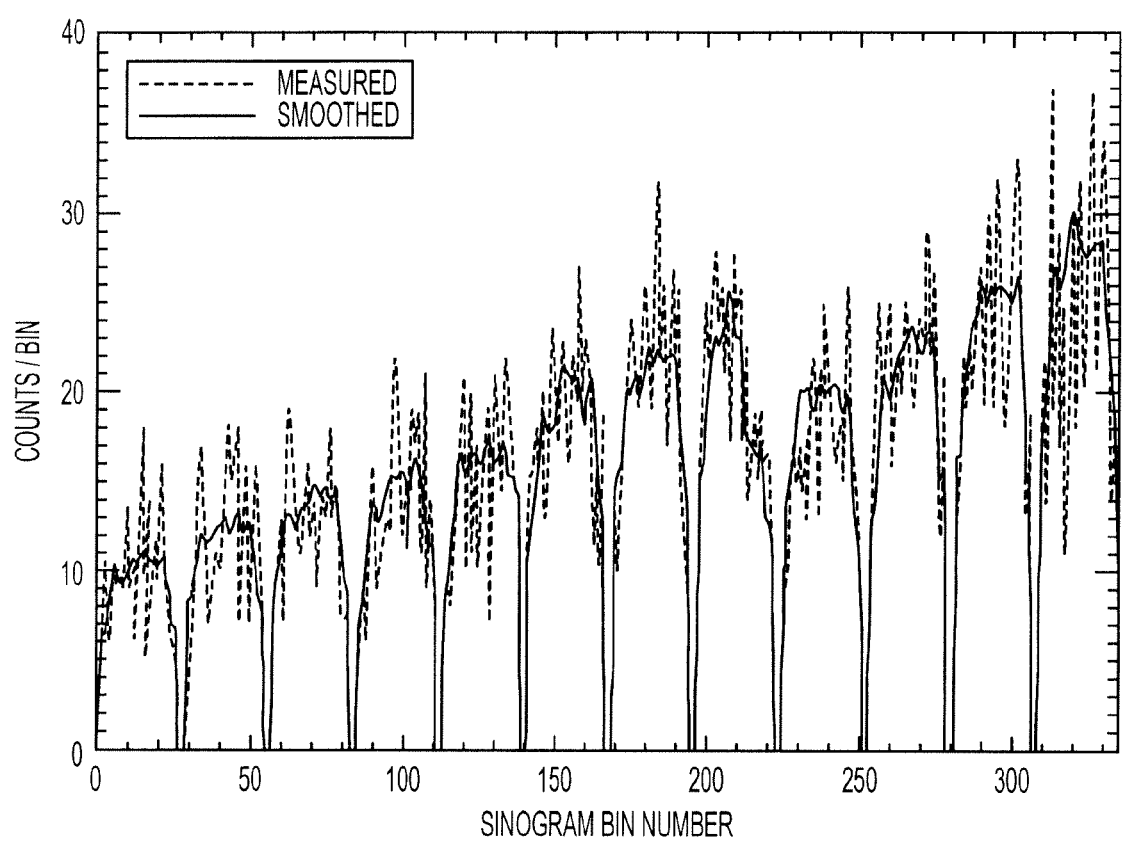
FIG. 5 shows a line chart of counts/bins over sinogram bin number comparing profiles along central rows of the two sinograms in FIGS. 3 and 4.

In a more specific embodiment a scan from a NEMA NU 2-2001 count rate test with a 70 cm long phantom, at high activity, was performed. The singles rate was 46.7 Mcps, and the randoms/net trues ratio was 2.4. One sinogram from this data set was considered. This measured delayeds (random coincidence) sinogram is shown in FIG. 3. The corresponding estimated smoothed randoms sinogram $R_{a,b}$ is shown in FIG. 4. The calculation of this smoothed sinogram took less than 1 second. As may be taken from the FIGS. 3 and 4, the estimated sinogram is less noisy than the measured sinogram. FIG. 5 shows a line chart of counts/bins over sinogram bin number comparing profiles along central rows of the two sinograms in FIGS. 3 and 4. As may be taken from the FIG. 5, the structure of the randoms distribution is accurately reproduced. The randoms per bin vary by a factor of 2.5 across the sinograms.

Figure 6:
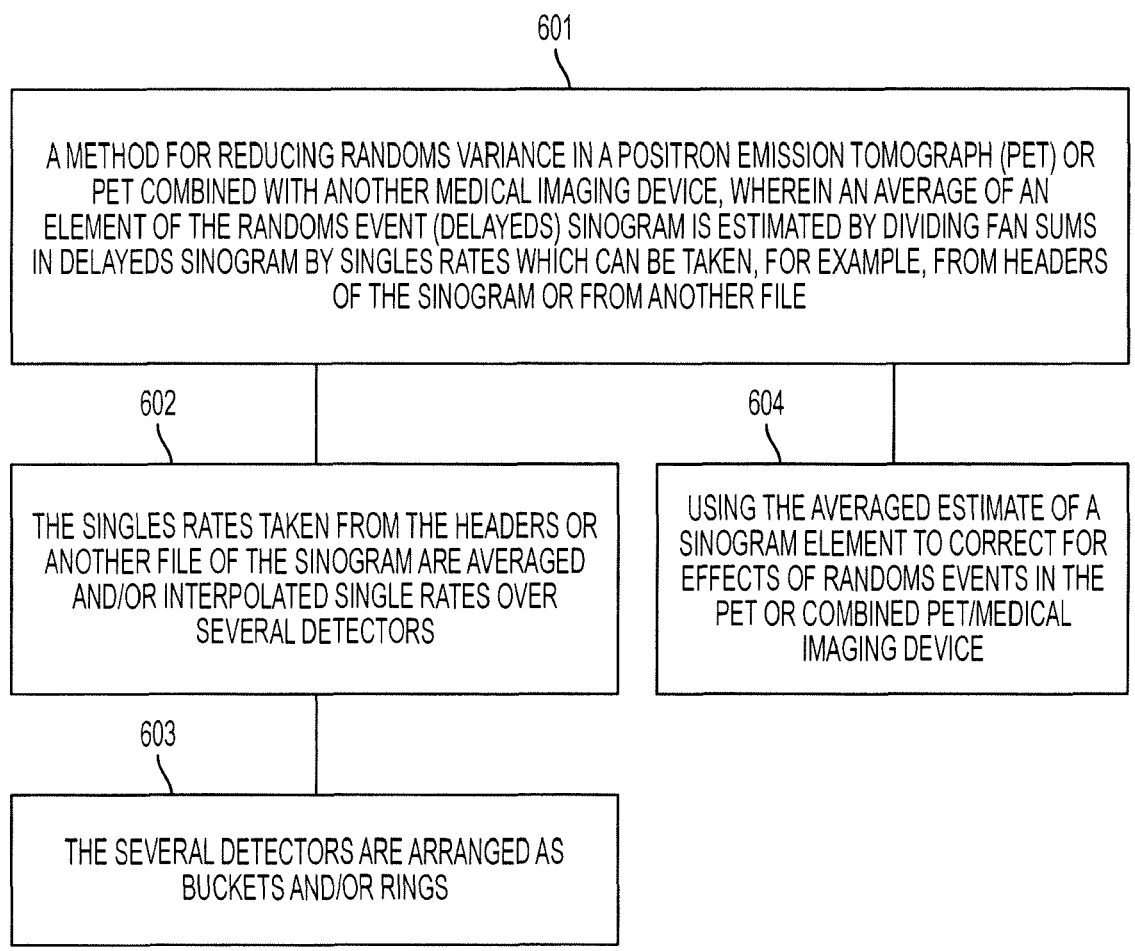
FIG. 6 is a flow chart of an exemplary embodiment of a method according to an embodiment.

According to one embodiment, a method may comprise the steps as outline in the flow chart in FIG. 6. The exemplary method for reducing randoms variance is suitable for use in a Positron Emission Tomograph (PET) or Positron Emission Tomograph combined with another Medical Imaging device such as an X-ray Computed Tomography scanner (PET/CT) or MRI device. As a first step, outlined in box 601, an average of an element of the randoms event (delayeds) sinogram is estimated by dividing fan sums in a delayeds sinogram by singles rates taken from the header of the sinogram.

The singles rates may be taken from the header of the sinogram in different ways, depending on the internal configuration of the PET, PET/CT or PET/MRI. As outlined in box 602, the singles rates taken from the header of the sinogram may be averaged and/or interpolated single rates over several detectors. These detectors may be arranged in a certain structure influencing the possibilities for how the singles rates are registered in the headers of the sinograms. According to box 603, the several detectors may be arranged as buckets and/or rings.

According to one embodiment a method may use the averaged estimate of a sinogram element to correct for effects of randoms events in the PET, PET/CT or PET/MRI. This is outlined in box 604.

At least one embodiment provides for a system and a method that allows for a more accurate and precise reduction of randoms variance. As mentioned above, the implementation of at least one embodiment allows for a fast computing for reducing random variance and consequently makes embodiments desirable from an economical and/or technical perspective.

The system and method discussed above reduces randoms variance. The invention, therefore, is well adapted to carry out the objects and attain the ends and advantages mentioned, as well as others inherent therein. While the invention has been described and is defined by reference to particular preferred embodiments of the invention, such references do not imply a limitation on the invention, and no such limitation is to be inferred. The invention is capable of considerable modification, alteration, and equivalents in form and function, as will occur to those ordinarily skilled in the pertinent arts. The described preferred embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. A method for reducing randoms variance in a Positron Emission Tomograph (PET) or Positron Emission Tomograph combined with another Medical Imaging device, wherein an averaged estimate of an element, $R_{ij}$, of a randoms event (delayeds) sinogram corresponding to detectors $i$ and $j$ in a detector ring of the PET or PET/Medical Imaging device is expressed as $$\hat{R}_{ij} = \frac{R_i R_j}{2\tau \left( \sum_{i' \in I_j} s_{i'} \right) \left( \sum_{j' \in J_i} s_{j'} \right)}$$

wherein
$R_i$ and $R_j$ are fan sums for detectors $i$ and $j$;
$2_T$ is the coincidence time window;
the randoms relate to single rates $s_i$ and $s_j$ in the detectors by
$R_{ij} = 2_T s_i s_j$;
$I_j$ is a set of detectors corresponding to the fan of detector $j$; and
$J_i$ is a set of detectors corresponding to the fan of detector $i$;
the method comprising the steps of:
estimating the numerator from fan sums in the delayeds sinogram of the PET or PET/Medical Imaging device;
estimating the denominator from recorded singles rates;
using the resulting averaged estimate of $R_{ij}$ as a randoms event (delayeds) sinogram.

2. The method according to claim 1, wherein the Medical Imaging device is an X-ray Computed Tomography scanner or a Magnetic Resonance Imaging (MRI) device.

3. The method according to claim 1, wherein the single rates are recorded in the header of the sinogram.

4. The method according to claim 3, wherein estimating the denominator from singles rates taken from the header of the sinogram comprises averaging or interpolating the single rates over several detectors.

5. The method according to claim 4, wherein the several detectors are arranged as buckets and/or rings.

6. The method according to claim 3, wherein estimating the denominator from singles rates taken from the header of the sinogram comprises averaging and interpolating the single rates over several detectors.

7. The method according to claim 6, wherein the several detectors are arranged as buckets and/or rings.

8. The method according to claim 1, the method further comprising the step of using the averaged estimate of $R_{ij}$ to correct for effects of randoms events in the PET or PET/Medical Imaging device.

9. A method for reducing randoms variance in a Positron Emission Tomograph (PET) or Positron Emission Tomograph combined with another Medical Imaging device, wherein an average of an element of a randoms event (delayeds) sinogram is estimated by dividing fan sums in the delayeds sinogram by recorded singles rates.

10. The method according to claim 9, wherein the Medical Imaging device is an X-ray Computed Tomography scanner or a Magnetic Resonance Imaging (MRI) device.

11. The method according to claim 9, wherein the single rates are taken from the header of the sinogram.

12. The method according to claim 11, wherein the singles rates taken from the header of the sinogram are averaged or interpolated single rates over several detectors.

13. The method according to claim 12, wherein the several detectors are arranged as buckets and/or rings.

14. The method according to claim 11, wherein the singles rates taken from the header of the sinogram are averaged and interpolated single rates over several detectors.

15. The method according to claim 14, wherein the several detectors are arranged as buckets and/or rings.

16. The method according to claim 9, the method further comprising the step of using the averaged estimate of the element to correct for effects of randoms events in the PET or PET/Medical Imaging device.

* * * * *

UNITED STATES PATENT AND TRADEMARK OFFICE
CERTIFICATE OF CORRECTION

PATENT NO. : 8,022,368 B2  Page 1 of 1
APPLICATION NO. : 12/121020
DATED : September 20, 2011
INVENTOR(S) : Charles C. Watson It is certified that error appears in the above-identified patent and that said Letters Patent is hereby corrected as shown below:

In the CLAIMS SECTION, Column 10, lines 1-3 (Claim 9, lines 4-6) after "event" should read
-- delayeds sinogram by measured single rates, and a resulting averaged estimate of said element
is used as a randoms event (delayeds) sonogram. --.

Signed and Sealed this
Third Day of January, 2012

David J. Kappos
*Director of the United States Patent and Trademark Office*